US00PP12601P2

(12) United States Plant Patent
Jauchen

(10) Patent No.: US PP12,601 P2
(45) Date of Patent: May 7, 2002

(54) MINIATURE ROSE PLANT NAMED 'KORPUSIRO'

(75) Inventor: Daniel E. Jauchen, Santa Barbara, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/553,089

(22) Filed: Apr. 19, 2000

(51) Int. Cl.[7] ..... A01H 5/00
(52) U.S. Cl. ..... Plt./122
(58) Field of Search ..... Plt./122, 116, 121

*Primary Examiner*—Bruce R. Campell
*Assistant Examiner*—June Hwu
(74) *Attorney, Agent, or Firm*—Klarquist Sparkman, LLP

(57) ABSTRACT

Miniature rose plant having a stable, deep pink flower color; ease of rooting from cuttings; rapid growth; good pot rose habit; and long shelf life.

1 Drawing Sheet

The present invention relates to a new and distinct variety of rose plant of the miniature class which was discovered as a single branch spontaneous flower color mutation on a rose plant of the variety 'KORhomapo' (U.S. Plant Pat. No. 11,148) in a greenhouse in Santa Barbara, Calif.

'KORpusiro' differs from 'KORhomapo' principally in flower color. 'KORpusiro' is a deep pink color mutation of 'KORhomapo', the flowers of which are red in color. Like 'KORhomapo', 'KORpusiro' is an ideal pot rose; easy to root from cuttings; grows rapidly; and has a good pot rose habit, long shelf life, and stable flower color.

Asexual reproduction of this new variety by cuttings, as performed at Somis and Santa Barbara, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage: Spontaneous mutation of 'KORhomapo' (U.S. Plant Pat. No. 11,148).

Classification:

*Botanical.*—*Rosa hybrida.*

*Commercial.*—Miniature rose.

FLOWER

Observations made from specimens six months of age grown in a greenhouse environment at Somis and Santa Barbara, Calif., January through November 1999.

Blooming habit: Continuous.

Bud:

*Size.*—¾ inch long when the petals start to unfurl.

*Form.*—The bud form is long; blunt topped.

*Color.*—When sepals first divide, bud color is Red Group 53D. When half blown, the upper sides of the petals are close to Red-Purple Group 60B; and the lower sides of the petals are Red Group 53D.

*Sepals.*—Color: Green Group 138B. Length: 1 inch to 1⅛ inches. Shape: Subulate. Surface texture: Covered in fine hairs. There are three lightly appendaged sepals. There are two unappendaged sepals with hairy edges.

*Receptacle.*—Color: Yellow-Green Group 146C. Shape: Funnel. Size: Small (about 7/32 inch×3/16 inch). Surface: Smooth.

*Peduncle.*—Length: Short (about 1¼ inches). Surface: Smooth with some small glands. Color: Green Group 137A. Strength: Stiff; erect.

Bloom:

*Size.*—Small. Average open size is about 2 to 2¼ inches.

*Borne.*—Singly and several together in flat clusters of three to five blooms.

*Stems.*—Strength: Strong. Average length is about eight to ten inches.

*Form.*—When first open: High centered. Permanence: Flattens; all petals curl.

*Petalage.*—Number of petals under normal conditions: 35 to 40.

*Color.*—The upper sides of the petals are Red-Purple Group 60B. The reverse sides of the petals are Red Group 53D. The base of each petal has a small, 3/16 inch×⅛ inch, White Group 155B half moon at the point of attachment. The major color on the upper side is Red-Purple Group 60B.

*Variegations.*—Occasional greenish-white streaks on the petals in the center of the flower.

*Discoloration.*—The general tonality at the end of the first day: No change. At the end of the third day: No change. No change until petal drop at day 11 or 12.

*Fragrance.*—None.

Petals:

*Texture.*—Thick. Smooth.

*Shape.*—Round.

*Margin.*—Entire.

*Apex.*—Mucronate.

*Base.*—Obtuse.

*Form.*—Tips slightly recurved.

*Arrangement.*—Imbricated. Petaloids in the center are many (up to 20 per flower) and small (⅛ inch to ¼ inch wide); same color as the petals.

*Persistence.*—Petals drop off cleanly before drying.

*Lastingness.*—On the plant: Long (about 11 to 12 days). As a cut flower: Very long (15 to 16 days).

Reproductive parts:

*Anthers.*—Length: About 1/16 inches. Quantity: Few. Color: Yellow-Orange Group 16B. Arrangement: Regular around styles; mixed with petaloids.

*Filaments.*—Color: Yellow-Orange Group 16A. Length: 1/4 inch–3/8 inch.

*Pollen.*—Color: Not observed.

*Styles.*—Color: Green-White Group 157B. Length: 3/16 inches–5/16 inches.

*Stigmas.*—Color: Green-White Group 157D.

*Pistils.*—Quantity: 60–80.

*Stamens.*—Quantity: 70–90.

*Hips.*—None observed.

Plant:

*Form.*—Bush.

*Growth.*—Vigorous; upright; branching. At maturity, height is three feet; width is 2½ feet in a garden setting. As a pot rose in a 6½ inch pot, height is 12 to 14 inches and width is 12 inches.

Foliage: Number of leaflets on normal mid-stem leaves: Five.

*Size.*—Small (3½ inches long×2½ inches wide).

*Quantity.*—Abundant.

*Color.*—New foliage: Upper and lower surfaces: Greyed-Red Group 178B. Old foliage: Upper surface: Green Group 137A. Lower surface: Green Group 137D.

Leaflets:

*Shape.*—Pointed oval.

*Texture.*—Leathery; glossy; upper and lower surface smooth with prominent veins on the lower surface.

*Edge.*—Serrated.

*Serration.*—Single; small.

*Petiole rachis.*—Color: Green Group 137C.

*Petiole color.*—Yellow-Green Group 145A.

*Stipules.*—Short (about ½ inch); serrated; bearded; smooth. Color: Green Group 137C.

*Disease resistance.*—Resistant to mildew and rust under normal growing conditions. Not tested for blackspot.

*Pest resistance.*—No pest resistance/susceptibility observed.

Wood:

*New wood.*—Color: Green Group 137C. Bark: Smooth.

*Old wood.*—Color: Green Group 137A. Bark: Smooth.

Prickles:

*Quantity.*—On main canes from base: Ordinary. On laterals from main canes: Ordinary.

*Form.*—Short (about 1/32 inch); straight.

*Color when young.*—Greyed-Purple Group 183C.

*Color when mature.*—Greyed-Orange Group 176D.

Small prickles:

*Quantity.*—On main stalks: None. On laterals: None.

*Hardiness.*—Hardy to Zone 5.

I claim:

1. A new and distinct variety of rose plant of the miniature class, substantially as herein shown and described, characterized particularly by it's stable, deep pink flower color; ease of rooting from cuttings; rapid growth; good pot rose habit; and long shelf life.

* * * * *

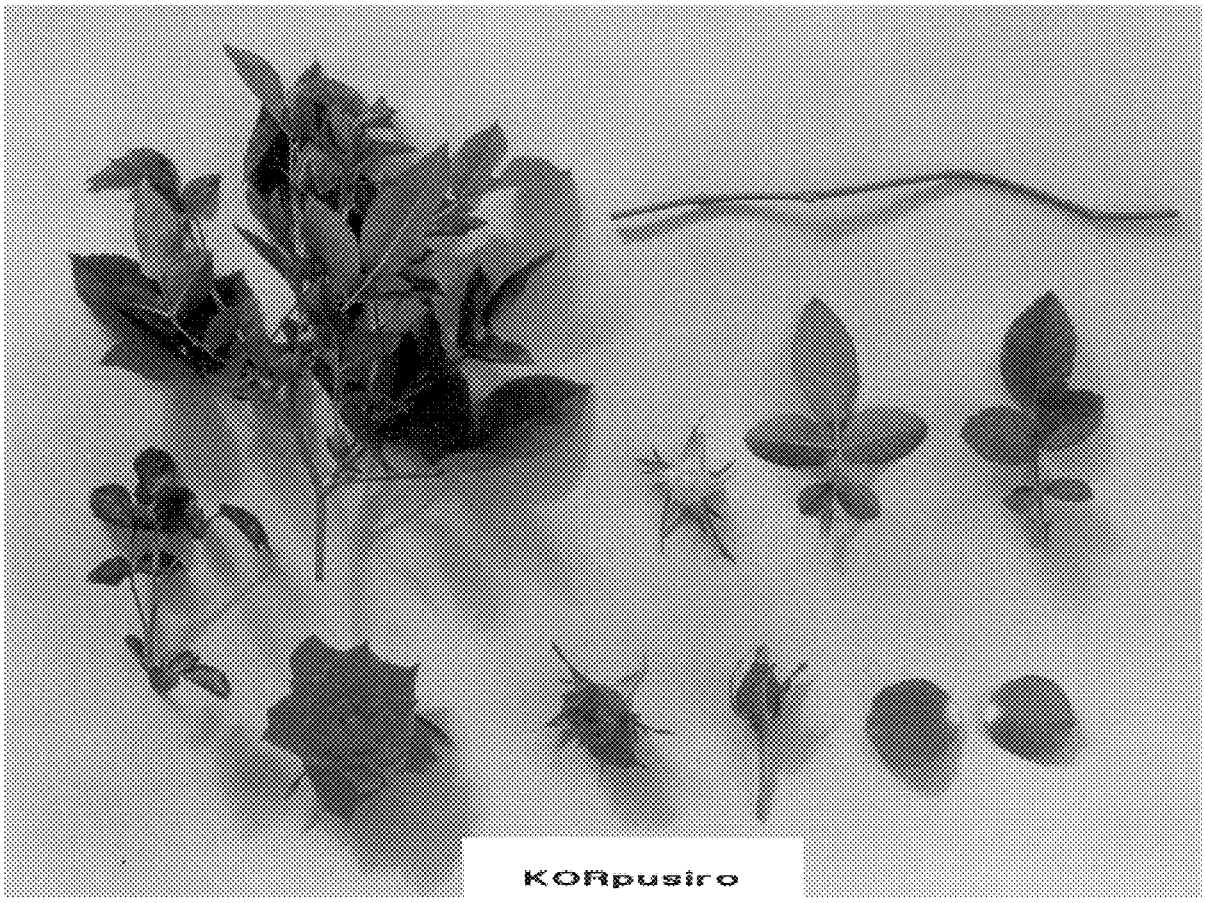
KORpusiro